United States Patent [19]

Clark et al.

[11] Patent Number: 5,741,973
[45] Date of Patent: Apr. 21, 1998

[54] SPRING RELEASE MECHANISM FOR ELECTROMAGNETIC ACOUSTIC TRANSDUCER (EMAT) PROBE

[75] Inventors: Steven Paul Clark, Bedford County; Daniel T. MacLauchlan, Lynchburg, both of Va.

[73] Assignee: The Babcock & Wilcox Company, New Orleans, La.

[21] Appl. No.: 394,683

[22] Filed: Feb. 24, 1995

[51] Int. Cl.⁶ .................................................... G01N 29/04
[52] U.S. Cl. .......................... 73/643; 324/219; 324/262; 33/DIG. 1
[58] Field of Search ................ 73/643; 324/220, 324/221, 219, 260, 262; 33/559, DIG. 1

[56] References Cited

U.S. PATENT DOCUMENTS

| | | | |
|---|---|---|---|
| 4,449,408 | 5/1984 | Brooks et al. | 73/643 |
| 4,510,447 | 4/1985 | Moyer | 324/225 |
| 4,769,598 | 9/1988 | Krieg et al. | 324/219 |
| 5,254,944 | 10/1993 | Holmes et al. | 324/220 |
| 5,514,956 | 5/1996 | Maxfield et al. | 324/262 |

*Primary Examiner*—Michael Brock
*Assistant Examiner*—Richard A. Moller
*Attorney, Agent, or Firm*—Robert J. Edwards; Eric Marich

[57] ABSTRACT

In an electromagnetic acoustic transducer or EMAT, a spring release mechanism comprises a frame or carriage and, if necessary at least one movement element for permitting movement across a surface of a workpiece. A magnet is movable against the surface past the frame or carriage and a base supports the magnet. The spring is connected between the frame and the base for biasing the base away from the frame to urge the magnet away from the surface.

20 Claims, 3 Drawing Sheets

SPRING RELEASE MECHANISM FOR ELECTROMAGNETIC ACOUSTIC TRANSDUCER (EMAT) PROBE

FIELD AND BACKGROUND OF THE INVENTION

The present invention relates, in general, to EMAT probes, and in particular, to a new useful spring release mechanism for the permanent magnet of such probes.

A transducer, known as an electromagnetic acoustic transducer or EMAT, requires a magnetic field to function. This field can be provided by a permanent magnet or an electromagnet. The permanent magnet is ideal for many applications because it eliminates the need for a power supply and can often occupy less space than an electromagnet. Generally, the EMAT is more effective if the magnetic field is high. However, when using a permanent magnet EMAT as, for example, an inspection transducer on ferromagnetic material, the EMAT can be difficult to remove from the inspected part due to the significant attraction force. Furthermore, the magnetic field can make it difficult to move the transducer on the part because of drag caused by high frictional forces.

The known methods for removing an EMAT transducer are, 1) brute force—exerting enough pull force on the transducer to overcome the magnetic attraction, 2) use of a wedge—by sliding the transducer up the wedge, the magnetic force is gradually overcome, and 3) twisting—in the case of a transducer that is contoured to fit a pipe and roll along the axis of the pipe, twisting the transducer 90° causes the surfaces to decouple. The third case is a special case and use of a wedge—the mating surfaces create the wedge effect.

It is common practice to design the transducer, or probe, with rolling elements, such as four wheels, to help overcome the drag caused by frictional forces.

SUMMARY OF THE INVENTION

Accordingly, one aspect of the present invention is to provide, in an electromagnetic acoustic transducer or EMAT, a spring release mechanism for facilitating removal of the transducer from a surface of a workpiece, comprising: a frame; magnet means movable against the surface past the frame; a base for supporting the magnet means for movement past the frame against the surface and for movement away from the surface; and biasing means connected between the frame and the base for biasing the base away from the frame to urge the magnet means away from the surface.

Yet another aspect of the invention is to provide at least one movement element on the frame for permitting movement of the frame across a surface.

Another aspect of the invention is to provide the biasing means with sufficient force so that it automatically disengages the magnet means from the surface when a pressure pushing the base toward the frame is released. A still further aspect of the invention is to provide the biasing means with such biasing force that only additional force will release the magnet means from the surface after the magnet means has been engaged to the surface.

A still further aspect of the invention is to provide the biasing means with such biasing force that the magnet means itself is sufficient to pull the magnet means into engagement with the surface against the biasing force of the biasing means.

A still further aspect of the invention is to provide a spring release mechanism for the magnet means, in particular, a permanent magnet of an EMAT probe, which is simple in design, rugged in construction and economical to manufacture.

The various features of novelty which characterize the invention are pointed out with particularity in the claims annexed to and forming a part of this disclosure. For a better understanding of the invention, its operating advantages and specific results and benefits attained by its uses, reference is made to the accompanying drawings and descriptive matter in which preferred embodiments of the invention are illustrated.

DESCRIPTION OF THE PREFERRED EMBODIMENTS

Figure 1A:
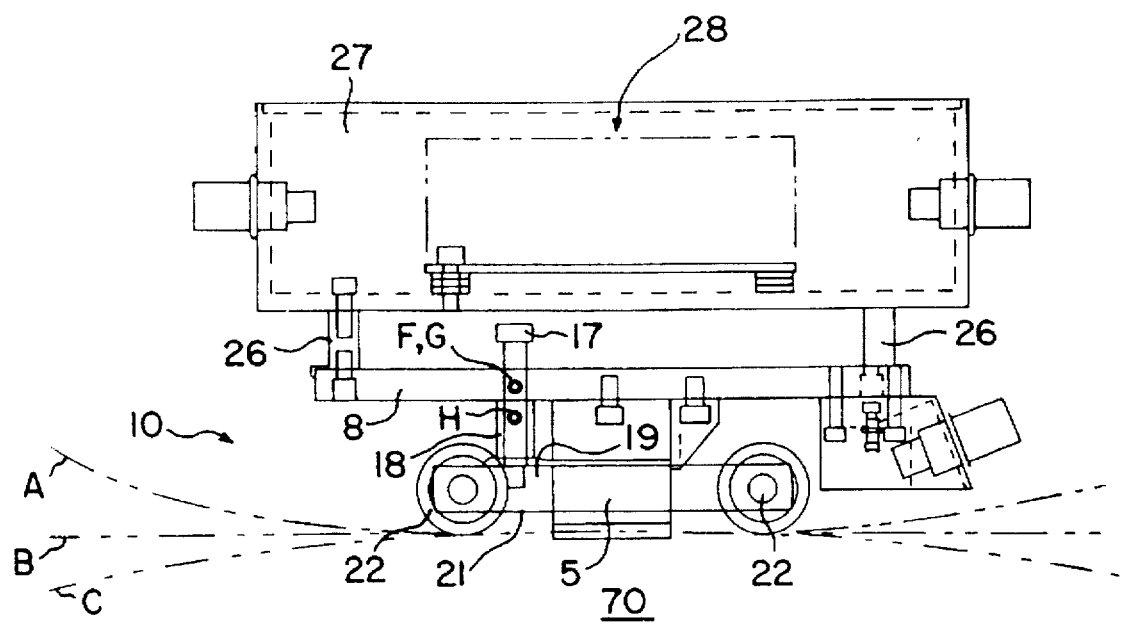
FIG. 1A is a side elevational view of one embodiment of the invention showing the EMAT arrangement on the spring release mechanism of the invention.
Figure 1B:
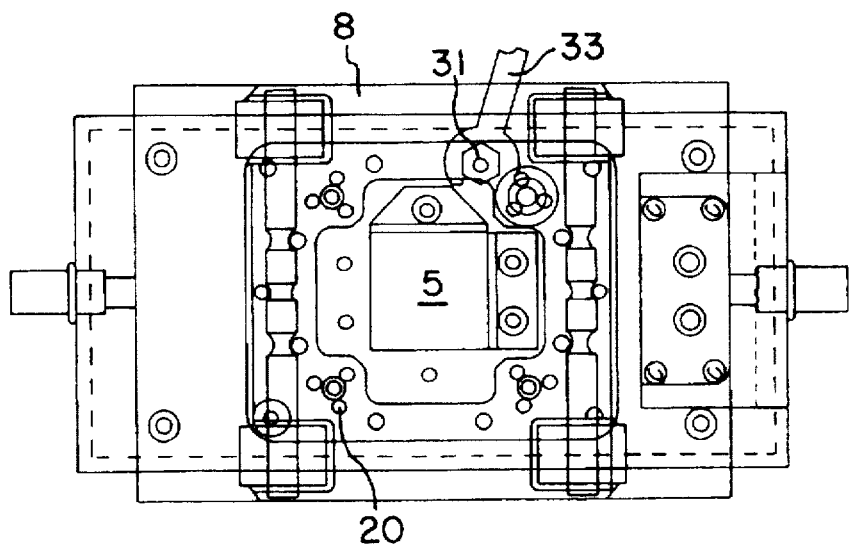
FIG. 1B is a top plan view thereof.

Referring to the drawings in particular, wherein like numerals designate the same or functionally similar elements throughout the several drawings, the invention embodied in FIGS. 1A and 1B comprises a spring release mechanism generally designated 10, for an EMAT probe having electronics 28 in a box 27 mounted by stand-offs 26, 26 to a base or base plate 8.

The present invention, which in short may be referred to as a spring release EMAT, reduces the amount of force required to remove an EMAT from a ferromagnetic material workpiece 70 without reducing the magnetic field. The workpiece 70 may have a concave, flat, or convex surface represented in FIG. 1A by the dotted lines designated A, B, C, respectively. The probe, shown in FIGS. 1A and 1B, is constructed by mounting a permanent magnet 5, to a base 8. The magnet 5 and base 8 are attached to a frame or carriage 21, by means of one or more biasing means 18. Advantageously, biasing means 18 can comprise one or several compression springs 18. These springs 18 are retained by shoulder screws 17, which project through the top of the base 8 to retain the base 8 to the frame or carriage 21. In this example, the frame or carriage 21 includes movement elements 22 such as rolling elements or wheels, but the frame or carriage 21 could use skids instead of, or in combination with, rolling elements 22. Such a construction is particularly desirable to facilitate rolling and/or sliding scan inspections of the workpiece 70. However, the spring release EMAT construction of the present invention could also be adapted to constructions where the EMAT is used for single point inspections. In such a case, neither skids nor rolling elements would be employed. The probe includes stops 31 (in this case screws), to control the final standoff distance between the magnet and the inspected material workpiece 70 by nuts on the stops that can be turned by a removable wrench 33. The EMAT coil is placed between the magnet 5 and the workpiece material. The final deflection of the springs 18 is adjustable—in this example, by means of a washer 19, between the springs 18 and frame or carriage 21 and several set screws 20, in the frame or carriage 21 which can be turned to adjust the washer 19.

Figure 2:
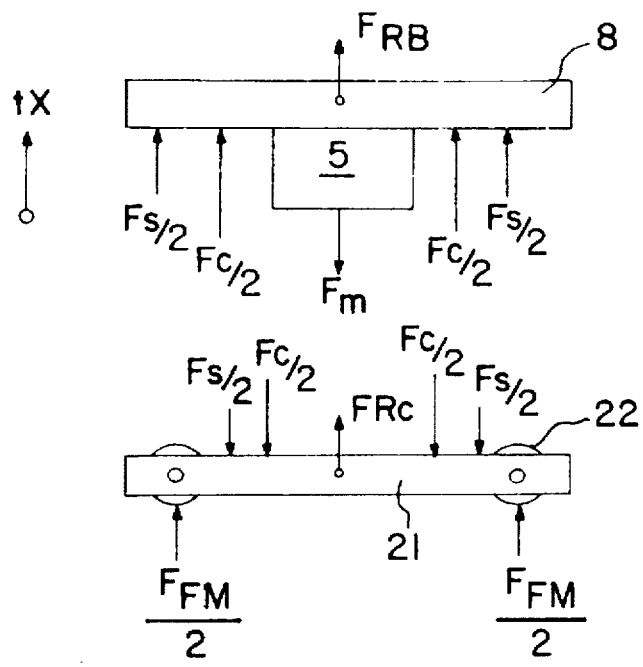
FIG. 2 is a side schematic representation showing the various forces exerted on the carriage and base of the mechanism.

When the probe is placed on a ferromagnetic material workpiece 70, an attractive force is created between the magnet 5 and the workpiece 70 and tries to pull the base plate 8 toward the workpiece 70. This force is countered by the springs 18 and increases as the springs 18 deflect. The force of the magnet 5 is transmitted by the springs 18 into the frame or carriage 21. Thus, the frame or carriage 21 receives the full force of the magnet 5 transmitted through the springs 18 so that if an attempt to remove the probe from the material at the frame or carriage 21 is made, the entire magnetic force of the magnet 5 must be overcome. However, since the springs 18 are opposing the magnetic force on the base plate 8, it is possible to pull the base plate 8 away from the workpiece 70 with less force than on the frame or carriage 21. The free body diagrams, shown in FIG. 2, illustrate the balance of forces on the frame or carriage 21 and the base plate 8, and are set forth below:

BASE PLATE $+\uparrow \Sigma F_X = 0 = F_{RB} + F_S + F_C - F_M$ (1.1)

or $F_M = F_{RB} + F_S + F_C$ (1.2)

$F_M = F_S + F_{RB}$ when $F_{RB} = 0$ (1.3)

$F_M = F_S + F_{RB}$ when $F_C = 0$ (1.4)

FRAME OR CARRIAGE $+\uparrow \Sigma F_X = 0 = F_{RC} - F_S - F_C + F_{FM}$ (2.1)

or, substituting 1.2 $O = F_{RC} - F_M + F_{FM} + F_{RB}$ (2.2)

$F_M = F_{RC} + F_{FM}$ (when $F_{RB} = 0$) (2.3)

$F_M = F_{FM}$ when $F_{RC} = 0$ (when $F_{RB} = 0$) (2.4)

$F_M = F_{RC}$ when $F_{FM} = 0$ (when $F_{RB} = 0$) (2.5)

Note $F_{RB} < F_M$ due to $F_S$ (Eq. 1.4)

But $F_{RC} = F_M$ (Eq. 2.5)

$F_S$=spring force;
$F_M$=magnet force;
$F_C$=reaction force from frame or carriage;
$F_{FM}$=reaction force from ferromagnetic material;
$F_{RB}$=removal force base plate;
$F_{RC}$=removal force frame or carriage; and
where weight effects are ignored.

It should be noted that the attractive force of the magnet 5 as a function of distance from the ferromagnetic material workpiece 70 is nonlinear, but the opposing force of the compression springs 18 is essentially linear as a function of distance. The performance of this spring mechanism depends on the initial and final deflections of the springs 18, the spring constant, and the magnetic force as a function of distance for a given magnet and ferromagnetic material. It is useful to know the magnetic force vs. distance and this is easily obtained experimentally. The spring parameters can be selected to result in a probe with one of these performance characteristics:

when the probe is placed on the workpiece 70, the magnet 5 compresses the springs 18 to final deflection with no external force applied, when the probe is placed on the workpiece 70 and an external force of sufficient magnitude is applied, the magnet and external force compress the springs 18 to final deflection and maintains this deflection when the external force is removed, and, when the probe is placed on the workpiece 70 and an external force of sufficient magnitude is applied, the magnet and external forces compress the springs 18 to final deflection but cannot maintain this deflection when the external force is removed.

Use of the spring release EMAT of the invention provides the following advantages over the prior art:

Reduces operator fatigue resulting from the effort required to apply and remove the EMAT probe to a ferromagnetic surface.

Reduces inspection time of the material by reducing the time and effort required to move the probe from location to location.

Permits the use of more powerful magnets than would otherwise be possible.

Can be applied to EMAT probes which use electromagnets as well as permanent magnets.

Reduces damage to the EMAT probe by allowing it to ride over an asperity more easily, reducing or preventing gouging or other damage to the face of the EMAT.

The specific compression spring design shown in FIG. 1A permits a range of performance which can easily be tailored to any given application by calculation and selection of the spring parameters.

In this invention, compression springs 18 store energy as the magnetic force compresses the springs. This invention could be constructed using any other energy storage device which in some fashion exerts force between the base plate 8 to which the magnet 5 is attached, and the inspected ferromagnetic material workpiece 70. These energy storage devices could include:

mechanical springs of any design, e.g. torsion, leaf, extension, belleville washers, other spring washers, constant force, plastic compression springs, etc.; and/or compressed air devices such as gas spring cylinders, air bladders, etc.

Figure 3:
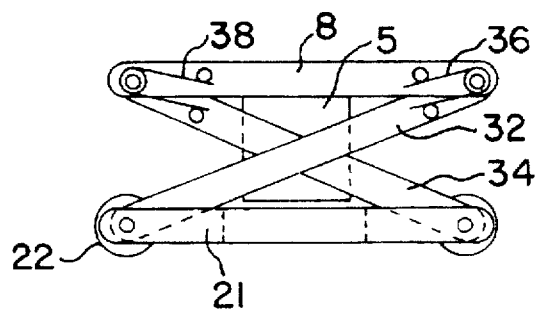
FIG. 3 is a side elevational view of another embodiment of the mechanism.
Figure 4:
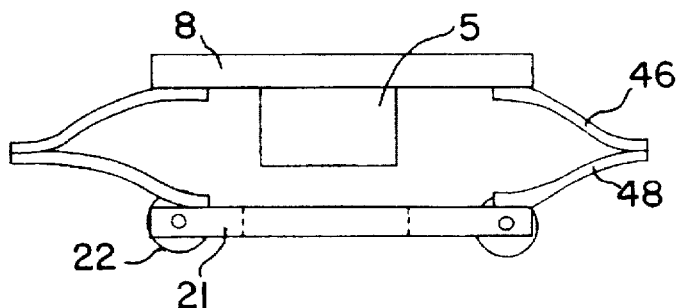
FIG. 4 is a view similar to FIG. 3 of a still further embodiment of the invention.
Figure 5:
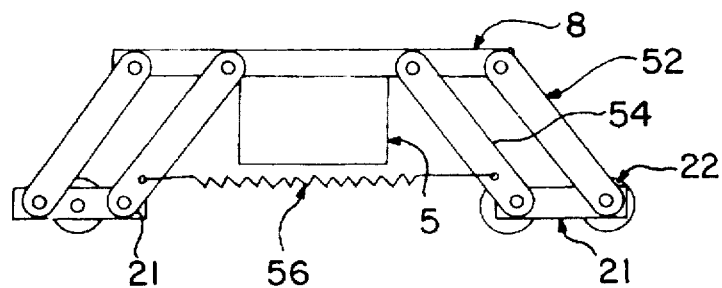
FIG. 5 is a view similar to FIG. 3 of another embodiment of the invention.
Figure 6:
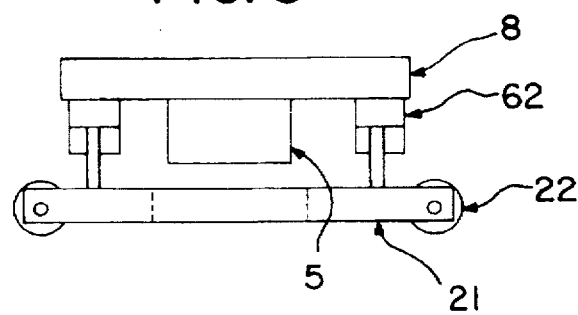
FIG. 6 is a view similar to FIG. 3 of a still further embodiment of the invention.

In this invention, the shoulder screws 17 retain the base plate 8 to the frame or carriage 21 and control the position of the base plate 8 relative to the frame or carriage 21. Other methods for attaching the base plate to the frame or carriage 21 and controlling the relative position of these two components is possible. FIG. 3 shows an alternative construction using link arms 32, 34 and torsion springs 36, 38. FIG. 4 shows an alternative using leaf springs 46, 48. FIG. 5 shows an alternative using link arms 52, 54 and extension springs 56 connected between two parts of the frame or carriage 21, 21. FIG. 6 shows an alternative using gas springs 62 as the spring and positioning mechanism.

In this invention, a washer 19 and set screws 20 provide adjustment of the compression spring. This adjustment could be made by other mechanical methods including shims, a single threaded ferrule under the spring 18, or other equivalent means.

Figure 7:
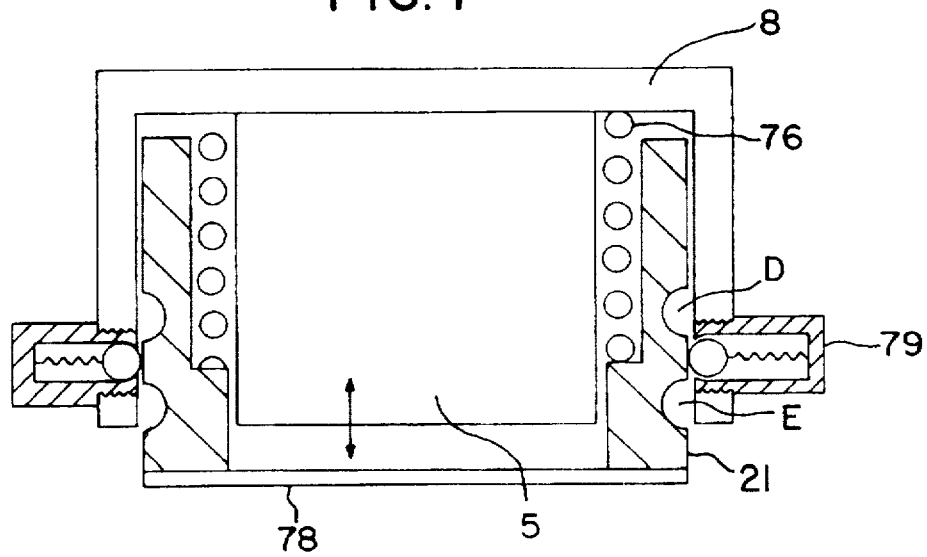
FIG. 7 is a view similar to FIG. 3 of yet a still further embodiment of the invention.

The base 8 and frame or carriage 21 are shown in FIGS. 1, 1A, 1B in a rolling configuration intended for moving across a surface. FIG. 7 replaces the base 8 and frame or carriage 21 with similar components intended for stationary use. The arrangement of FIG. 7 also shows spring means 76 as coaxial to the magnet means 5. In this example, the EMAT coil 78 is shown attached to the frame or carriage 21 such that the magnet means 5 retracts away from the EMAT coil 78.

It may be desirable to provide locating means wherein the magnet means, once engaged into a functional working position adjacent to the surface of the workpiece, 70 to permit an inspection thereof, can be locked into position. Locking means such as a ball detent, set screw, or straight pin would suffice. The locking means preferably locks the base 8 to the frame or carriage 21 (rather than engaging the magnet 5 directly). Alternatively, the locking means could be used to secure the magnet 5 at a non-functional working position away from the surface of the workpiece 70.

FIG. 7 shows one example of locking means where ball detent 79 may engage with either non-functional working position D or functional working position E. Likewise, FIG. 1A shows locking pin holes G and H which are part of shoulder screw 17 which is fixed to the frame or carriage 21. Hole F is found in the base 8. When a locking pin (not shown) is engaged through hole F into hole G, the probe is locked into a functional working position. When the same locking pin is engaged through hole F into hole H, the probe is locked into anon-functional working position.

Besides permanent magnets, at least two other magnet types are commonly used in EMAT devices—the DC electromagnet and the pulsed magnet. This invention is also useful with the DC electromagnet. In the case of the pulsed magnet, the invention offers little value since the pulsed magnet does not typically generate a continuous attractive force. In the case of the DC electromagnet, the invention is unlikely to be applied since it is usually a simple matter to switch Off the electromagnet, thus removing the magnetic attractive force. However, there may be special applications where it is desirable to use the invention with the DC electromagnet, and such applications are clearly within the definition of magnet means as used in this disclosure, and therefore within the scope of the present invention. Furthermore, it is possible to imagine applications which combine two or more of the magnet types, in which case the invention would also apply.

While specific embodiments of the invention have been shown and described in detail to illustrate the application of the principles of the invention, it will be understood that the invention may be embodied otherwise without departing from such principles.

We claim:

1. In an electromagnetic acoustic transducer, a spring release mechanism for facilitating removal of the transducer from a surface of the workpiece, comprising:

a frame;

magnet means movable against the surface past the frame;

a base for supporting the magnet means for movement past the frame against the surface and for movement away from the surface;

compression spring biasing means connected between the frame and the base for biasing the base away from the frame to urge the magnet means away from the surface; and means, connected between the compression spring biasing means and the frame, for adjusting a final deflection of the compression spring biasing means and thus an opposing force produced thereby.

2. The mechanism of claim 1, wherein said biasing means provides an opposing force with respect to an attractive force produced by the magnet means which automatically disengages the magnet means from the surface when an external force applied to the base pushing the base toward the frame is removed.

3. The mechanism of claim 1, wherein said biasing means provides an opposing force with respect to an attractive force produced by the magnet means and an additional external opposing force applied to the base is required to release the magnet means from the surface after the magnet means has been engaged to the surface.

4. The mechanism of claim 1, wherein said biasing means has such biasing force that the magnet means itself is sufficient to pull the magnet means into engagement with the surface against the biasing force of the biasing means.

5. The mechanism of claim 1, wherein the biasing means comprise at least one gas spring engaged between the frame and the base.

6. The mechanism of claim 1, wherein the magnet means comprises a permanent magnet.

7. The mechanism of claim 1, wherein the magnet means comprises a DC electromagnet.

8. The mechanism of claim 1, wherein the frame is a carriage further comprising movement element means on the carriage for permitting movement of the carriage along a surface of the workpiece.

9. The mechanism of claim 8, wherein the movement element means comprises at least one rolling element to allow the carriage to roll along the surface of the workpiece.

10. In an electromagetic acoustic transducer, a spring release mechanism for facilitating removal of the transducer from a surface of a workpiece, comprising:

a frame;

magnet means movable against the surface past the frame;

a base for supporting the magnet means for movement past the frame against the surface and for movement away from the surface; and biasing means including a pair of cross-linked arms pivotally mounted between the base and the frame and at least one torsion spring engaged between at least one of the base and frame and at least one of the linked arms, for providing a biasing force for biasing the base away from the frame to urge the magnet means away from the surface.

11. In an electromagnetic acoustic transducer, a spring release mechanism for facilitating removal of the transducer from a surface of a workpiece, comprising:

a frame;

magnet means movable against the surface past the frame;

a base for supporting the magnet means for movement past the frame against the surface and for movement away from the surface; and biasing means including a pair of frame elements comprising the frame, a pair of link arms pivotally mounted between each frame element and the base, and an extension spring connected between the frame elements for biasing the frame elements toward each other for moving the base away from the frame elements to urge the magnet means away from the surface.

12. In an electromagnetic acoustic transducer, a spring release mechanism for facilitating removal of the transducer from a surface of a workpiece, comprising:

a carriage having movement element means thereon for permitting movement of the carriage along a surface of the workpiece, the movement element means including at least one skid element to allow the carriage to slide along the surface of the workpiece;

magnet means movable against the surface past the carriage;

a base for supporting the magnet means for movement past the carriage against the surface and for movement away from the surface;

compression spring biasing means connected between the carriage and the base for biasing the base away from the carriage to urge the magnet means away from the surface; and means, connected between the compression spring biasing means and the carriage, for adjusting a final deflection of the compression spring biasing means and thus an opposing force produced thereby.

13. In an electromagnetic acoustic transducer, a spring release mechanism for facilitating removal of the transducer from a surface of a workpiece, comprising:

a carriage having movement element means thereon for permitting movement of the carriage along a surface of the workpiece, the movement element means comprising a combination of at least one rolling element and at least one skid surface to allow the carriage to roll and slide along the surface of the workpiece;

magnet means movable against the surface past the carriage;

a base for supporting the magnet means for movement past the carriage against the surface and for movement away from the surface;

compression spring biasing means connected between the carriage and the base for biasing the base away from the carriage to urge the magnet means away from the surface; and means, connected between the compression spring biasing means and the carriage, for adjusting a final deflection of the compression spring biasing means and thus an opposing force produced thereby.

14. In an electromagnetic acoustic transducer, a spring release mechanism for facilitating removal of the transducer from a surface of a workpiece, comprising:

a frame;

magnet means movable against the surface past the frame;

a base for supporting the magnet means for movement past the frame against the surface and for movement away from the surface;

biasing means connected between the frame and the base for biasing the base away from the frame to urge the magnet means away from the surface; and locking means for securing the base to the frame to position the magnet means at a desired locked position with respect to the surface of the workpiece.

15. The mechanism of claim 14, wherein the locking means positions the magnet means at a functional working locked position adjacent the surface of the workpiece to permit an inspection of the workpiece.

16. The mechanism of claim 14, wherein the locking means positions the magnet means at a non-functional locked position away from the surface of the workpiece.

17. The mechanism of claim 14, wherein the locking means comprise one of a bail detent, set screw and straight pin.

18. In an electromagnetic acoustic transducer, a spring release mechanism for facilitating removal of the transducer from a surface of the workpiece, comprising:

a frame;

magnet means movable against the surface past the frame;

a base for supporting the magnet means for movement past the frame against the surface and for movement away from the surface; and leaf spring biasing means connected between the frame and the base for biasing the base away from the frame to urge the magnet means away from the surface.

19. In an electromagnetic acoustic transducer, a spring release mechanism for facilitating removal of the transducer from a surface of the workpiece, comprising:

a frame;

magnet means movable against the surface past the frame;

a base for supporting the magnet means for movement past the frame against the surface and for movement away from the surface; and at least one compression spring biasing means assembled coaxially around the magnet means and connected between the frame and the base for biasing the base away from the frame to urge the magnet means away from the surface.

20. In an electromagnetic acoustic transducer, a spring release mechanism for facilitating removal of the transducer from a surface of the workpiece, comprising:

a frame;

magnet means movable against the surface past the frame;

a base for supporting the magnet means for movement past the frame against the surface and for movement away from the surface, the base and frame assembled coaxially around the magnet means; and at least one compression spring biasing means assembled coaxially around the magnet means and connected between the frame and the base for biasing the base away from the frame to urge the magnet means away from the surface.

* * * * *